United States Patent [19]

Hochberg

[11] Patent Number: 4,549,553
[45] Date of Patent: Oct. 29, 1985

[54] APPARATUS AND METHOD FOR USE IN A MEDICAL GAS SAMPLING SYSTEM

[75] Inventor: Howard M. Hochberg, Woodinville, Wash.

[73] Assignee: Spacelabs, Inc., Chatsworth, Calif.

[21] Appl. No.: 549,027

[22] Filed: Nov. 7, 1983

[51] Int. Cl.$^4$ ............................................. A61B 5/08
[52] U.S. Cl. ................................... 128/719; 128/730; 128/205.12
[58] Field of Search ............... 128/719, 730, 718, 716, 128/207.14, 205.12

[56] References Cited

U.S. PATENT DOCUMENTS

| 3,661,528 | 5/1972 | Falk | 128/719 X |
| 4,456,014 | 6/1984 | Buck et al. | 128/719 |
| 4,485,822 | 12/1984 | O'Connor et al. | 128/719 |

OTHER PUBLICATIONS

Holness et al., Med. Instrum., vol. 9, No. 1, Jan.-Feb. 1975, pp. 23-25.

Primary Examiner—Kyle L. Howell
Assistant Examiner—John C. Hanley
Attorney, Agent, or Firm—Lawrence S. Levinson; Robert E. Lee, Jr.

[57] ABSTRACT

An apparatus and method for providing a sample gas flow from an air tube of a patient undergoing automatic ventilation is disclosed. The air tube includes a gas diffusive membrane disposed in a wall of the air tube. The base of a funnel member is disposed to engage the air tube at the membrane, the area of the base substantially equal to the area of the membrane. The funnel member includes a tubular end portion opposite the base which end portion is disposed to be coupled to a sampling tube or gas monitoring equipment. Cross sectional area of the tubular end portion is substantially smaller than the area of the base. A pump in the gas monitoring system is coupled to the tubular end portion and causes a small portion of the gas in the air tube to pass through the membrane into the funnel. The velocity of the sample gas flow through the membrane is lower than the velocity through the tubular end portion but the sample gas flow rate remains constant. The gas diffusive membranes can be non-wettable membranes for rejecting water from entering the sample gas flow. Sampling tubes coupled between the tubular end portion and the gas monitoring system may also comprise water absorbing or water passing materials to eliminate excess water from the gas sample flow.

6 Claims, 3 Drawing Figures

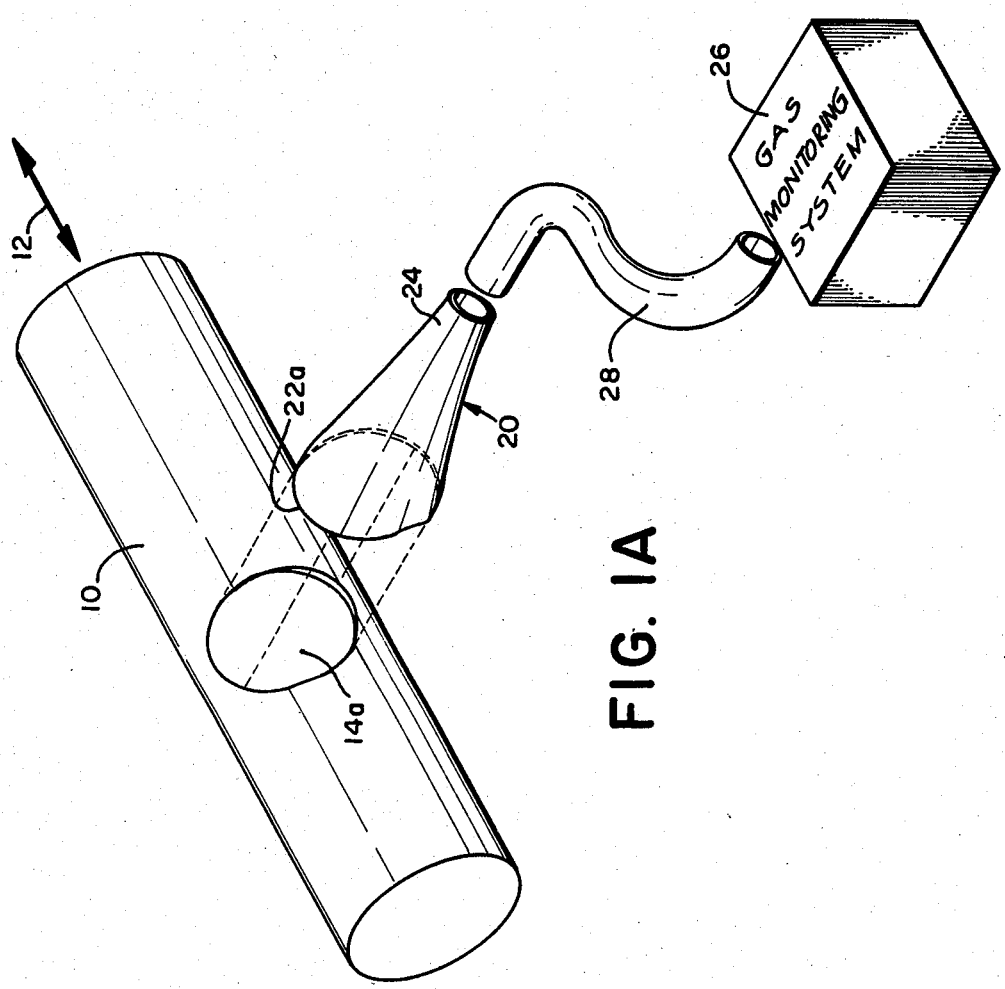

APPARATUS AND METHOD FOR USE IN A MEDICAL GAS SAMPLING SYSTEM

BACKGROUND OF THE INVENTION

This invention relates to the field of medical gas sampling, more particularly for protecting medical gas sampling devices from contamination, obstruction and interfering substances.

Some patients receiving automatic ventilation through an artificial air tube are monitored for respiratory problems by drawing a small sample flow of gas from the air tube and continuously analyzing the level of carbon dioxide (capnography) or other gases. Typically, a sampling tube is used to convey the sampled flow of gas from the air tube to the gas monitoring means, the diameter of the sampling tube being small compared to the diameter of the air tube.

Ventilated patients in the Intensive Care Unit (ICU) commonly have pulmonary problems with many secretions such as copious viscous sputum. These secretions are thixotropic gels which can and do solidify and adhere to a variety of surfaces, including the plastics used in medical tubing such as sampling tubes used in gas monitoring devices.

In order to draw gas from the air tube, a vacuum is applied to one end of the sampling tube using for example a pump in the gas monitoring device. This usually causes relatively high gas velocities to occur in the sampling tube which in turn frequently causes the above mentioned secretions to enter the small diameter gas sampling tube of capnographs and similar devices where they may partially or completely obstruct air flow. Secretions may also enter the small sensitive optical sensing chamber of the capnograph devices and interfere with measurements.

Clinicians claim that capnograph type devices are not useful in the ICU environment because the above mentioned problems make it necessary to clear the instrument or tubes as often as every 20 minutes. While surgery patients usually have no pulmonary problems, and they receive drugs which dry the secretions, nevertheless, their air way gases contain anesthetic agents which can also distort the gas analysis.

SUMMARY OF THE INVENTION

It is an object of the present invention to provide an improved apparatus and method for providing a sample gas flow for medical gas monitoring.

It is a further object of the present invention to prevent secretions and other solid and liquid contaminants from entering the sampling tube and sensing chambers of capnographs and similar gas sensing devices.

A further object of the present invention is to reduce the tendency of secretions and other solid and liquid contaminants to migrate toward and accumulate near the orifices of sampling tubes within the air way tubes of patients undergoing automatic ventilation.

Accordingly, an apparatus for obtaining a sample gas flow from an air tube of a patient undergoing automatic ventilation comprises a gas diffusive membrane disposed within a wall of an air tube, and a funnel having a base, the base disposed such that the interior of the air tube is enabled to communicate with the interior of the funnel through the gas diffusive membrane.

The funnel further comprises a tubular shaped end portion which is opposite the base of the funnel. The cross section of the tubular end portion is substantially smaller than either the cross section of the base or the gas diffusive membrane. In the preferred embodiment the area of the membrane is substantially equal to the area of the base of the funnel. The gas monitoring means comprises a pump which is coupled to the tubular end portion of the funnel for drawing the sample gas from the air tube through the membrane into the interior of the funnel. Because the cross section of the base is considerably larger than the cross section of the tubular end, the velocity of the gas flow through the base in substantially less than the velocity of the gas through the tubular end.

According to another aspect of the invention, a method for sampling the gas flow of an air tube of a patient undergoing automatic ventilation comprises the step of drawing a sample portion of the gas flow through a funnel member having a base disposed such that the interior of the air tube is enabled to communicate with the interior of the funnel. The method further comprises reducing the water content of the sample gas flow.

Further details and advantages of the invention will be apparent from the following specification and accompanying drawings, wherein:

BRIEF DESCRIPTION OF THE DRAWINGS

FIG. 1A is an exploded diagrammatic view of an alternate embodiment of the present invention of FIG. 1.

DETAILED DESCRIPTION OF THE DRAWINGS

Figure 1:
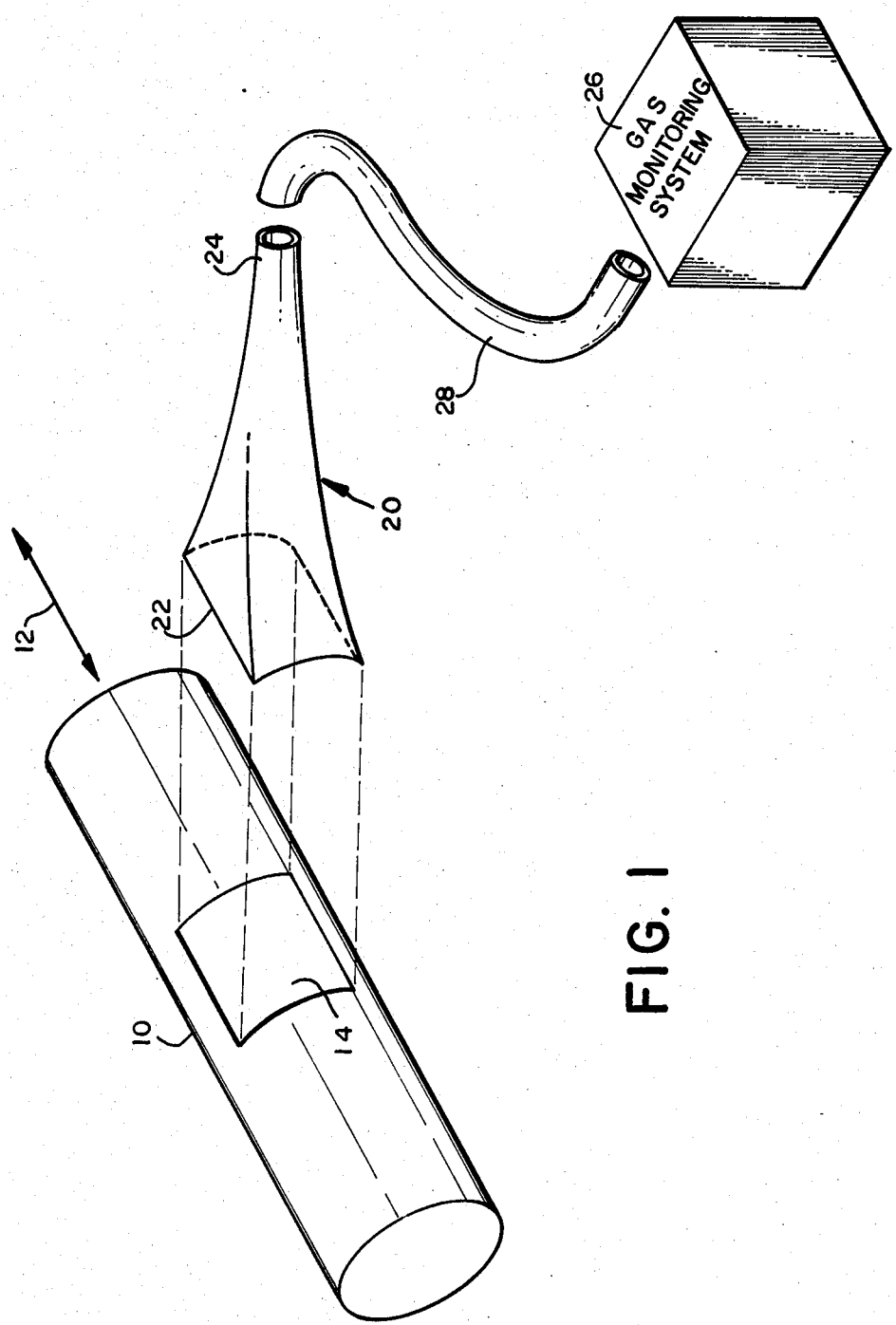
FIG. 1 is an exploded diagrammatic view of a preferred embodiment of the present invention.
Figure 2:
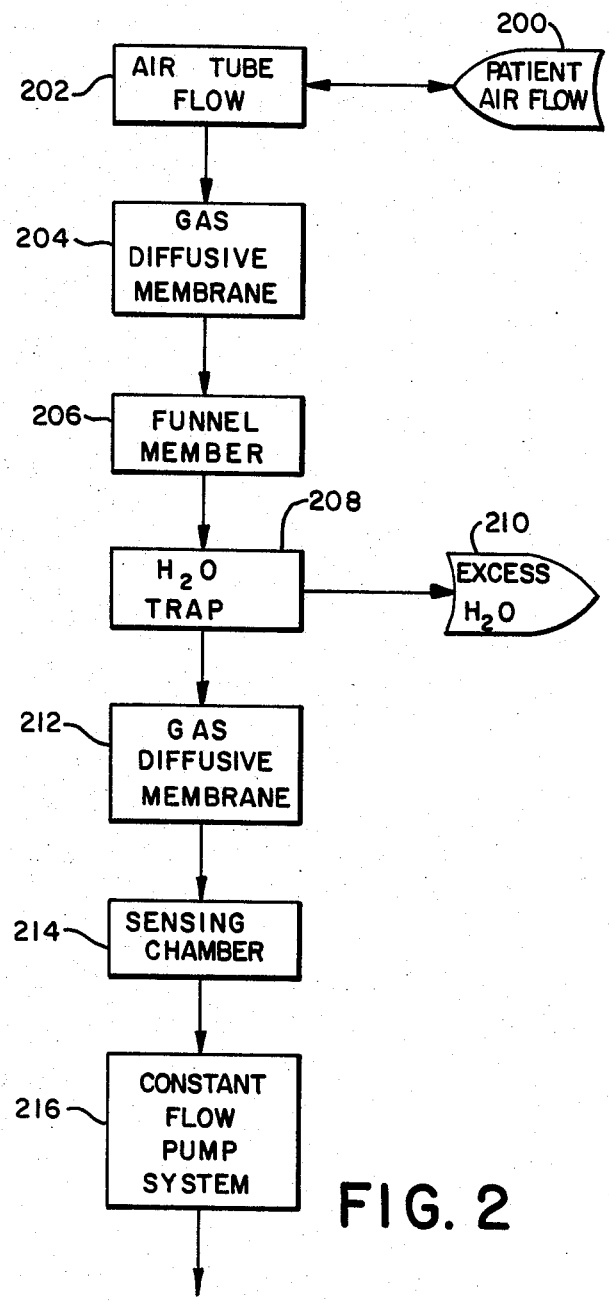
FIG. 2 is a block diagram flow chart of the process of carrying out the steps of the present invention.

Referring now to FIG. 1, a portion of an air tube 10 is illustrated for conducting the air flow of a patient undergoing automatic ventilation. The direction of the air flow back and forth within the air tube is indicated by the double arrow 12. Air tubes for this use are common in medicine and usually made of plastic tubing.

Unlike prior art air tubes used in medicine air tube 10 includes a gas diffusive membrane 14 disposed within the wall of the air tube 10 and having a relatively large area. A funnel member designated generally 20 is also shown having a base 22, the funnel member 20 shown separated from air tube 10 for clarity. In the preferred embodiment the base and membrane areas are substantially equal and rectangular in shape, and the base of the funnel member engages air tube 10 at membrane 14 such that the interior of air tube 10 communicates with the interior of funnel 20 through membrane 14. Membrane 14 and base 22 could be circularly shaped such as the membrane 14a and base 22a in FIG. 1A. The funnel further includes a tubular end portion 24 opposite the base. The cross sectional area of the tubular end portion 24 is considerably smaller than the cross sectional area of the base 22.

Tubular end portion 24 in the preferred embodiment is disposed to be coupled to a commercially available gas monitoring system 26 such as a Puritan Bennett Co. capnograph. Usually a sampling tube 28 connects the tubular end portion 24 to the gas monitoring equipment. A pump within the gas monitoring system creates a vacuum within the interior to the funnel which causes air or gases from within the air tube to be drawn through the gas membrane 14 into the interior of the funnel and then through the sampling tube to the gas monitoring equipment.

In order for the gas monitoring equipment to operate accurately a constant gas flow rate through the sampling tube is required. In the prior art, the sampling tube with a relatively small cross sectional area is coupled directly to the air tube and the velocity of the gas flow into the sampling tube orifice at the air tube interface is relatively high in order to accomodate the gas flow rate. This high velocity flow creates a tendency for secretions present in the air flow to enter the sampling tube and/or to travel down the tube and to enter the small sensitive optical measuring chamber of the gas monitoring device which then interferes with the measurement.

If the velocity of the sample gas flow leaving the air tube is lowered so that disturbance of the air flow within the air tube in the direction of arrows 12 is minimized then the tendency for secretions, etc. to enter the sample air flow will be lowered or eliminated. This is accomplished without decreasing the gas flow rate required by monitoring equipment by increasing the area at the air tube through which the sample gas flow moves. For example, the sample gas flow rate, Q, is the volume of gas which flows per unit time. It is related to the area perpendicular to the gas flow and the velocity of the gas flow as follows:

$$Q=A_mV_m=A_tV_t$$

where $A_m$ is the area of the membrane, $V_m$ is the velocity of the gas flow through the membrane. $A_t$ is the cross sectional area of the tubular end portion 24 and $V_t$ is the velocity of the gas flow through the tubular end portion. As $A_m$ increases, $V_m$ decreases to keep Q constant.

Hence, placing the funnel member 20 intermediate the air tube 10 and a sampling tube 28 for the gas monitoring equipment 26 causes a lower velocity of the sample gas flow through the membrane 14 for a given constant Q relative to the velocity of the gas flow which would be encountered at the orifice of a conventional sampling tube intersecting the air tube for the same Q. This lowers the amount of secretions entering the sample gas flow.

In the preferred embodiment, the gas diffusive membrane should be non-wettable to prevent or reduce water from entering the sample gas flow; otherwise, water saturates the membrane and water eventually passes through the membrane to enter the sample gas flow. This disturbs the accuracy of the measurements made by the gas monitoring equipment. By non-wettable it is meant that the membrane resists or cannot be saturated with liquid and its surfaces resists or cannot be covered with liquid. A Teflon® mesh membrane is a suitable non-wettable membrane. Teflon® is a registered trademark of DuPont Corporation of Wilmington Del. Teflon® is a plastic tetrafluroethylene homo polymar. A fifteen (15) micron pore Teflon mesh is a suitable mesh made by Gore Co. under the name Goretex.

FIG. 2 is a block diagram flow chart describing the various steps of the preferred embodiment method of providing a sample gas flow for medical gas monitoring purposes. The method comprises: providing a patient undergoing automatic ventilation with a two directional air flow through an air tube 200 and 202; drawing a sample of the air flow (usually less than 1%) through a gas diffusive membrane disposed in the side of the air tube 204, the membrane having a relatively high surface area (relative to the cross sectional area of a conventional sampling tube); drawing said sample gas flow through an intermediate funnel member 206, the base disposed to engage the air tube at the membrane, the funnel having a tubular end portion disposed opposite the base; eliminating excess water which may be present in the sample gas flow by drawing said gas flow through a water absorbing or water passing sampling tube coupled to the tubular end portion of the intermediate funnel member 208 and 210; and passing the sample gas flow through a second gas diffusive member before entering the sensing chamber of the gas monitoring equipment 212 and 214. The gas diffusive membranes may be gas selective membranes which reject selected gases from entering the sample gas flow and the sensing chamber. Constant gas flow is insured by a constant flow pumping system provided in the gas monitoring equipment 216.

Many changes and modifications in the above-described embodiment of the invention can of course be carried out without departing from the scope thereof. Accordingly that scope is intended to be limited only by the scope of the appended claims.

What is claimed is:

1. An apparatus for obtaining a sample gas flow from a patient undergoing automatic ventilation comprising:

an air tube;

a gas diffusive membrane disposed within the wall of said air tube;

a funnel comprising:

a base coupled directly to said air tube such that the interior of said air tube communicates with the interior of said funnel through said gas diffusive membrane; and a tubular shaped end portion opposite said base and disposed to be coupled to a gas monitor, the cross section of said tubular shaped end portion being substantially smaller than the cross section of said base.

2. The apparatus of claim 1 wherein said gas diffusive membrane comprises a non-wettable membrane whereby water is rejected from said sample gas flow.

3. The apparatus of claim 2 wherein said gas diffusive membrane comprises a Teflon mesh membrane.

4. The apparatus of claim 1 wherein said base has a substantially rectangular cross section.

5. The apparatus of claim 1 wherein said base has a substantially circular cross section.

6. The apparatus of claim 1 wherein said apparatus further comprises a pump coupled to said tubular end portion of said funnel for drawing said sample gas flow through said membrane such that the velocity of said gas flow through said base of said funnel is substantially less than the velocity at said tubular shaped end portion.

* * * * *